United States Patent [19]
Steinitz

[11] 3,937,967
[45] Feb. 10, 1976

[54] ELECTRONIC AIR PURIFIER WITH OZONE SUPPRESSION

[76] Inventor: Kurt Steinitz, 7 Kingswood Road, Danbury, Conn. 06810

[22] Filed: Apr. 16, 1974

[21] Appl. No.: 461,409

[52] U.S. Cl. ............................... 250/435; 250/436
[51] Int. Cl.² ........................................ G01N 21/24
[58] Field of Search .......... 250/432, 434, 435, 436, 250/437, 492; 21/74 R, 74 A, 53, 102 R, DIG. 2, 54 R

[56] References Cited
UNITED STATES PATENTS

| | | | |
|---|---|---|---|
| 3,403,252 | 9/1968 | Nagy | 250/432 X |
| 3,674,421 | 7/1972 | Decupper | 250/432 X |

*Primary Examiner*—Davis L. Willis

[57] ABSTRACT

An electronic air purifying method and apparatus whereby the air to be purified is introduced into the apparatus and oxygen molecules of said air are first transformed into the allotropic form of oxygen by a low pressure mercury ultra violet radiating device and then said allotropic form of oxygen is decomposed to nascent oxygen by heat. The so created nascent oxygen oxidizing instantaneously impurities contained in the air moving through the air purifying apparatus.

4 Claims, 4 Drawing Figures

ELECTRONIC AIR PURIFIER WITH OZONE SUPPRESSION

PRIOR ART

My invention relates to air purifiers and more particularly to an electronic air purifier which utilizes a low pressure mercury lamp for purposes of purification of air in a room.

In the prior art such devices are known as "ozonaires". The working principle of an "ozonair" is based on the electronic energy radiated in the ultra violet light spectrum by a low pressure mercury lamp. One well known ultra violet radiator in this group is a germicidal lamp type G4S11, manufactured by General Electric. Such germicidal lamps are designed to produce ultra violet radiations in the 2537 Angstroms wavelength and in the 1849 Angstroms wavelength.

SUMMARY OF THE INVENTION

It is an object of my invention to provide an improved method and apparatus to utilize the 1849 Angstroms wavelength of such a low pressure mercury lamp for air purification in a room.

Another object of my invention is to provide an apparatus in which the low pressure mercury lamp is so arranged that the germicidal effect on the room air passing through the apparatus is relatively large but where the area outside the apparatus is completely shielded against the germicidal radiation.

The primary object of my invention is to provide an air purifying device which utilizes a low pressure mercury lamp and which has the ability to control the creation, the break down, and the release of ozone.

In the prior art ozonaires ozonize the air and then release the air-ozone mixture into the room air, and it is claimed that the released ozone will eliminate unpleasant and disagreeable odors in the room. In praxis such an effect can be observed, but there is a definite disadvantage in having an appreciable amount of ozone in the air of a room at any time. The ozone might collect there to an undesirable or even toxic level.

I have found that the generally held view that ozone is the purifying medium is a misconception. It is rather the decomposition product of ozone, namely the oxygen atom, which is responsible for the observed effect. In room air of approximately 70°F ozone can linger for a long time. At such a temperature ozone deteriorates very slowly.

It is therefore an object of my invention to provide an improved method and apparatus which will permit the purification of the air in a room with an ozone producing low pressure mercury lamp without releasing uncontrolled quantities of ozone into the room air. In my apparatus ozone is efficiently created at ideal temperature, and said ozone is broken down to nascent oxygen in a controlled manner within the air purifying device itself, and therefore an undesirable accumulation of ozone within the room air is prevented. The advantage of such a device over an "ozonaire" is obvious.

Further objects of my invention are to provide an electronic air purifying device which operates uniformly and absolutely quietly, and in which the components that have to be replaced after a useful life can be exchanged easily without the use of tools and by unskilled hands.

Still further objects and advantages of my method and apparatus will appear from the following description and from the exemplifying embodiment of my invention, from the appended claims, and from the accompanying drawing in which:

Figure 1:
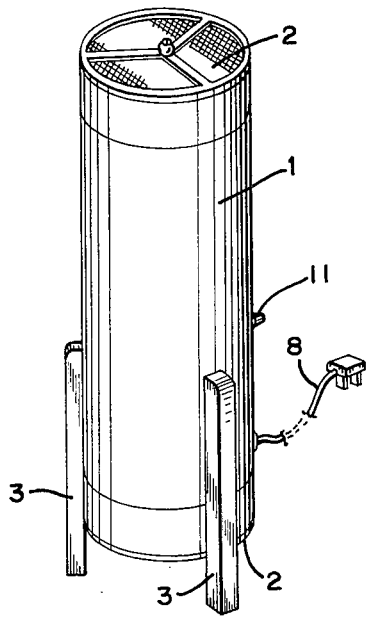
FIG. 1 shows my apparatus with an opaque housing in perspective view.

Referring to FIG. 1 of the drawing in details: an air purifying device is shown comprising a tubular housing 1 which is opaque to visual and ultra violet light, filters 2 inserted in the top and the bottom of said housing and legs or brackets 3 fastened to said housing for the purpose of elevating said tubular housing 1 to allow air to enter through the bottom filter 2 of said housing 1.

Figure 2:
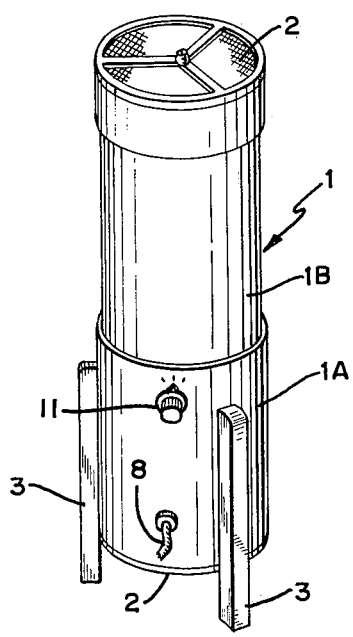
FIG. 2 shows my apparatus with a partially translucent housing in perspective view.

Referring to FIG. 2 of the drawing in details: shown is a similar housing as in FIG. 1 with the distinction that the housing 1 consists of a lower section 1A which is preferably made from an opaque material and an upper section 1B which is preferably partially made from a material translucent to visual light but opaque to ultra violet light.

Figure 3:
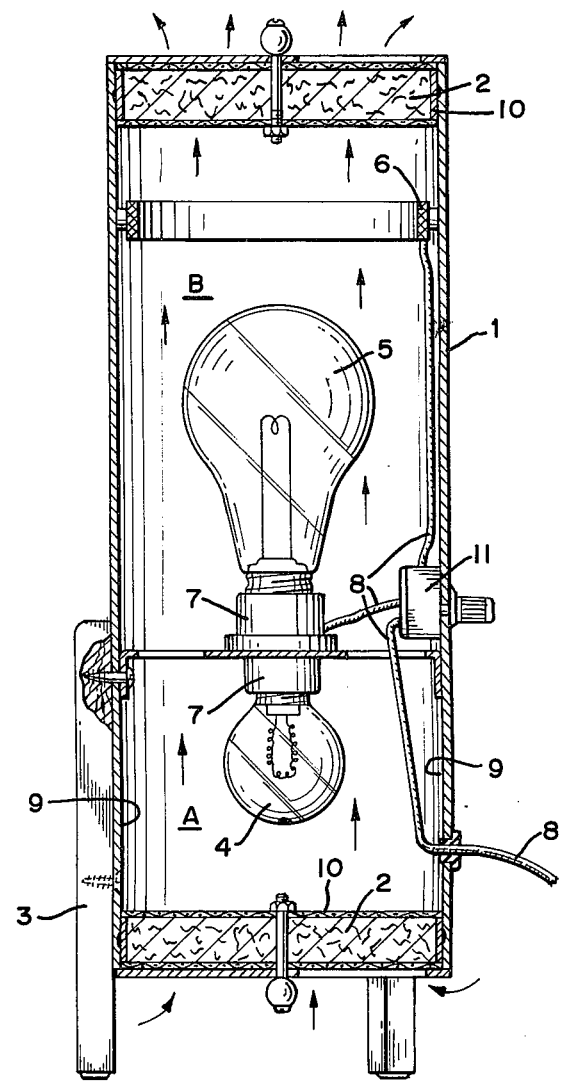
FIG. 3 shows a cross-sectional view of my apparatus.

Referring to FIG. 3 of the drawing in details: shown is a cross-sectional view of an air purifying device with a housing 1 of tubular form with an inner horizontal cross-section smaller than its inner vertical cross-section and so constructed that air heated inside the housing 1 will rise in said housing and create an air convection flow through said housing 1, a feature which is known as a "chimney effect". The inner walls of said housing 1 in its lower section A have a surface 9 which is highly reflective for the ultra violet radiation at the 2537 Angstroms wavelength. Filters 2 are inserted in the top and bottom of the tubular housing 1. Said filters 2 are preferably made from glass fibers and are held in frames 10 which can be snapped in said housing 1 by a simple push and which can be snapped out by a simple pull. In place, said filters 2 will allow air to flow freely through the housing 1 and in permitting the air to pass, the filters 2 will retain any coarse air-borne particles and said filters 2 are made dense enough to prevent ultra violet radiation, which is absorbed by the glass fibers, to escape to the outside of the housing. A low pressure mercury lamp 4 mounted in the lower section A of said housing 1, and a heater 5, which may be an ordinary incandescent light bulb, and an auxiliary heater 6 both mounted in the upper section B of said housing 1 above the low pressure mercury lamp 4. Electrical wiring 8 to connect the low pressure mercury lamp 4, the heater 5 and the heater 6 to an electrical power supply line.

Figure 4:
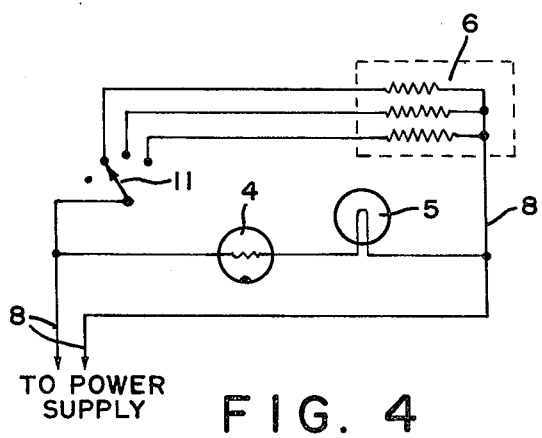
FIG. 4 shows an electric circuit diagram of my apparatus.

The heater 5 is preferably so dimensioned that it can serve in known manner as a load resister or ballast for the low pressure mercury lamp 4. The auxiliary heater 6 is dimensioned to allow its surface temperature to be set or regulated up to 600°F. As heater 6 I prefer a tapped wire or band heater which is mounted on the inner walls in the upper section B of the housing 1 and which can be regulated by a step switch 11. The heater 5 and the low pressure mercury lamp 4 are connected electrically preferably in series. Socket 7 is a double socket which contains means for the type of electrical connection as shown in FIG. 4 of the drawing. This socket arrangement permits the low pressure mercury lamp 4 and the heater 5 to be exchanged easily after removing the filters 2.

Utilizing for instance the germicidal lamp G4S11 as an ultra violet radiator 4 the heater 5 may be a 40 Watt light bulb on an electrical supply line of 115 Volts, and in this case the peak glass surface temperature of the bulb will be approximately 400°F inside the housing 1. On a 220 Volts electrical supply line the heater 5 may be a 75 Watt light bulb which will operate with a glass surface temperature of approximately 460°F inside the housing 1.

Having described an exemplifying embodiment of my air purifying device I will point out in the following its mode of operation: When heater 5 and low pressure mercury lamp 4 are activated, the heat created by the heater 5 will cause an air convection flow through the housing 1 as illustrated by the arrows in FIG. 3 of the drawing. The replacement air, room air of ambient temperature enters through the bottom filter 2 and passes in proximity of the low pressure mercury lamp 4. In passing a strong dose of radiation of germicidal wavelength impinges on the air. The highly reflective surface 9 on the inner walls in the lower section A of the housing 1 enhances the effect of this radiation. In my exemplifying embodiment the average distance at which the air has to pass the ultra violet radiator 4 is approximately one inch and at a distance of one inch the radiation intensity of the low pressure mercury lamp 4GS11 at the germicidal wavelength is greater than 1.5 Watts/sq.ft., an intensity great enough to exert a strong germicidal impact on the passing air.

At the same time the 1849 Angstroms wavelength transfers energy to some oxygen molecules ($O_2$) of the air and creates the allotropic form of oxygen, namely ozone molecules ($O_3$). The radiation energy of the 1849 Angstroms wavelength changes three stable molecules of oxygen ($O_2$) into two less stable ozone molecules ($O_3$). This transformation is performed in the lower part A of my air purifying device rather easily, because here the air temperature is always approximately 70°F. The air-ozone mixture flowing upwards is replaced by new incoming air of ambient temperature. Under such steady temperature condition a low pressure mercury lamp will produce stable radiation at the proper wavelengths.

The air-ozone mixture moves upwards after being created in the lower radiation zone A. Due to the fact that ozone is heavier than air a certain turbulence takes place during this upwards movement. A homogeneous mixture of air and ozone arrives in the upper section B of the air purifying device. In said section B of the housing 1 ozone is forced to break down by the infrared energy of the heaters in said section B. The ozone ($O_3$) distributed within the heated air decomposes to nascent oxygen ($O_1$). The oxygen atom ($O_1$) by its nature has to react almost instantaneously. In this moment impurities (for instance, odors) are oxidized and disappear from the air. The process is a continuous one; As long as the device is activated room air will be moved through its housing 1 and air will be purified by the germicidal wavelength and by the nascent oxygen, the decomposition product of the ozone created by the 1849 Angstroms wavelength in the lower section A and broken down by heat in the upper section B of the housing 1.

My method and apparatus make air purification of room air efficient and safe. Ozone is rather stable up to a temperature of 212°F. Above this temperature ozone decomposes rapidly. I have found that at a heater surface temperature of 400°F most of the ozone in my device is broken down and at 600°F all ozone has deteriorated. The auxiliary heater 6 in my device will allow one to set the temperature for any level of ozone decomposition. Inside the housing 1 the actual temperature of the air in the housing reaches a somewhat higher degree than the temperature that is transferred to the air by the heaters. When the ozone ($O_3$) breaks down in its components of three oxygen atoms ($O_1$) the energy that was originally needed to form the ozone molecule is released as heat. Oxygen can appear in three possible modes: (1) The stable oxygen molecule ($O_2$), which is our breathable oxygen normally contained in air. (2) The allotropic form of oxygen ($O_3$) known as ozone which can be created from $O_2$ by ultra violet radiation energy. (3) The oxygen atom ($O_1$) also known as nascent oxygen, which is created in my device by heat decomposition of ozone ($O_3$) and which has only a short life of $4 \times 10^{-6}$ sec. The short life characteristic, after its creation, of nascent oxygen ($O_1$) is the working principle of my device.

If all odors in the upper section B are oxidized, the surplus oxygen atoms combine in pairs with each other and form stable oxygen molecules. After the air taken in from the room through the lower filter 2 has passed through the device, the top filter 2 will expel into the room purified air enriched with newly formed stable oxygen molecules ($O_2$) and deprived of odors and ozone. I have found that in practical use a heater 5 alone without activating the auxiliary heater 6 is already sufficient to break down ozone within the device to a degree which will prevent any accumulation of ozone in the room air. I have found also that my air purifier will remove odors and will limit the amount of micro organisms in room air to a desirable level, whereby the length of time needed to operate the device depends on the size of the room. The auxiliary heater 6 can be set and can be regulated in such a manner as to prevent the escape of any ozone from the device into the room.

I desire it understood that my invention is not confined to the particular embodiment shown and described, the same being only illustrative. My invention may be carried out in other ways within the scope of the appended claims without departing from its spirit.

Having described the nature of my invention, what I claim and desire to protect by Letter Patent is:

1. An apparatus for purifying and sterilizing the air in a space and for decomposing ozone within said air comprising; a tubular housing having top and bottom sections with a horizontal cross section smaller than its vertical cross section and comprising a flow path for air and air-ozone mixtures; an air inlet in said bottom section and air outlet in said top section; an ultra violet radiating device placed in said bottom section of said housing in proximity to said air inlet for creating within said bottom section ozone in air of ambient temperature, and for emitting germicidal radiation; a heating device placed in said top section of said housing above said ultra violet radiating device for heating and decomposing ozone in said air-ozone mixture, and for supporting air flow through said tubular housing; means for connecting said ultra violet radiating device and said air heating device to an electric power supply; means for regulating the temperature of said heating device and of said air-ozone mixture in said top section of said housing; the air flow path in said housing comprising in the bottom section a germicidal radiation and ozone forming region and in the top section an ozone decomposing, impurities oxidizing and molecular oxygen forming region.

2. An apparatus for purifying and sterilizing the air in a space and for decomposing ozone within said air as in claim 1, said tubular housing including a removable inlet filter covering the bottom of said tubular housing and a removable outlet filter covering the top of said tubular housing, said filters preferably comprised of ultra violet radiation energy absorbing fiber material permitting unhampered in-and-out flow of air.

3. An apparatus for purifying and sterilizing the air in a space and for decomposing ozone within said air as in claim 2 wherein said bottom section is of material opaque to visual light and to ultra violet radiation, and said upper section is translucent to visual light and opaque to ultra violet radiation.

4. A method of purification and sterilization of air by exposing said air to ultra violet radiation followed by application of heat, whereby air of ambient temperature and with ambient amounts of ozone and impurities is first exposed to ultra violet radiation in the 2537 Angstroms wave band and in the 1849 Angstroms wave band; the 2537 Angstroms wave length having a sterilizing effect and the energy of the 1849 Angstroms wave band transforming oxygen molecules in said air into the allotropic form of oxygen, ozone; creating a continuously flowing and turbulent air-ozone-impurities mixture, which thereafter is exposed to heat; said heat decomposing the ozone molecules in said air-ozone-impurities mixture to nascent oxygen; said nascent oxygen practically instantaneously reacting with impurities by oxidizing them and at the same time reacting with neighboring oxygen atoms to form new stable oxygen molecules.

* * * * *